(12) United States Patent
Henry

(10) Patent No.: US 7,396,549 B2
(45) Date of Patent: Jul. 8, 2008

(54) METHOD FOR PRODUCING OENOLOGICAL TANNINS AND ENZYMATIC COMPOSITION

(75) Inventor: Olivier Henry, Nil Saint-Vincent (BE)

(73) Assignee: ETS. Robert Stiernon, S.A., Petit-Enghien (BE)

( * ) Notice: Subject to any disclaimer, the term of this patent is extended or adjusted under 35 U.S.C. 154(b) by 806 days.

(21) Appl. No.: 10/220,173

(22) PCT Filed: Mar. 2, 2001

(86) PCT No.: PCT/BE01/00033

§ 371 (c)(1),
(2), (4) Date: Aug. 28, 2002

(87) PCT Pub. No.: WO01/64830

PCT Pub. Date: Sep. 7, 2001

(65) Prior Publication Data

US 2003/0054056 A1    Mar. 20, 2003

(30) Foreign Application Priority Data

Mar. 3, 2000    (BE) .................................. 2000/0174

(51) Int. Cl.
*A23L 1/00* (2006.01)
(52) U.S. Cl. .............................. 426/52; 426/49; 426/615
(58) Field of Classification Search .................. 426/11, 426/12, 18, 44, 49, 52, 590, 592, 615
See application file for complete search history.

(56) References Cited

U.S. PATENT DOCUMENTS 4,251,668 A * 2/1981 Leaute ........................ 560/69
5,054,381 A * 10/1991 DePeaux et al. ........... 99/277.1
5,356,641 A * 10/1994 Bowen et al. ................. 426/52
6,623,953 B1 * 9/2003 Olivier ........................ 435/267

FOREIGN PATENT DOCUMENTS

| DE | 292864 | 8/1991 |
| EP | 0727493 | 8/1986 |
| EP | 0307071 | 3/1989 |
| WO | WO 98/44189 | 10/1994 |
| WO | WO 00/40382 | 7/2000 |

OTHER PUBLICATIONS

Techtips. 1997. http://www.eutechinst.com/techtips/tech-tips42.htm.*
Cornell. May 10,1999. http://web.archive.org/web/19991111203656/http://www.ansci.cornell.edu/plants/toxicagents/tannin/chemical.html.*
Abstract of Japanese Patent JP 50024405 A, dated Mar. 15, 1975 from Derwent Publications Ltd., London. GB: AN 1977-91378Y. XP002138537 (Japan Plywood Tech).

* cited by examiner

*Primary Examiner*—Leslie Wong
(74) *Attorney, Agent, or Firm*—Olson & Cepuritis, Ltd.

(57) ABSTRACT

The invention concerns an enzymatic method for making oenological tannins starting with lumps of wood and an enzymatic method for transforming tannins into tannins for winemaking purposes. The inventive method comprises a step which consists in contacting the lumps of wood or tannins with an aqueous solution comprising a composition containing enzymes of the cellulase class. The invention also concerns an enzymatic composition mainly consisting of enzyme of the cellulase class for making oenological tannins, comprising an endocellulase activity, a xylanase activity a β-mannanase and/or α-amylase activity.

12 Claims, No Drawings

METHOD FOR PRODUCING OENOLOGICAL TANNINS AND ENZYMATIC COMPOSITION

This application is the National Stage of International Application Ser. No. PCT/BE01/00033, which was filed on Mar. 2, 2001.

The present invention relates to an enzymatic method for producing oenological tannins starting with lumps of wood, to an enzymatic method for transforming tannins into tannins for oenological use, and also to an enzymatic composition for producing oenological tannins.

According to the International oenological codex, oenological tannin is drawn either from nutgall or from a tannin-rich wood (chestnut, oak) or from grapeseeds, etc. Tannin is composed of a mixture of glucosides, of ellagic acid, of gallic acid, of catechol, etc.

STATE OF THE ART

Methods for preparing tannins have, in the past, essentially been based on methods of extraction from plant products.

Thus, U.S. Pat. No. 4,490,405 uses an aqueous-alcoholic mixture, in variable proportions, to extract hop tannins. After the tannins have been recovered, the ethanol is recycled.

Other methods, such as EP 0 444 163 or WO 99/49129, use water at various temperatures between 60 and 100° C. to treat tree bark or wood particles for the purpose of extraction. It should be noted that tree bark cannot provide oenological tannins.

In WO 99/21634, the temperature used is even higher (115° C.) since the use of steam under pressure (0.3 MPa) is disclosed.

These methods, the use of which remains complex, do not allow very high yields to be obtained.

DESCRIPTION OF THE INVENTION

The aim of the present invention is to provide a method for extracting and transforming tannins enzymatically, in order to increase extraction yields and to enzymatically transform certain molecules having astringent or bitter characteristics into molecules with a more acceptable taste.

A subject of the invention is a method for extracting oenological tannins from lumps of wood, preferably sawdust, woodchips or mixtures of both, which are brought into contact, by immersion, with a bath, preferably an aqueous or aqueous-alcoholic bath, which mainly comprises a composition of enzymes of the hydrolase class (International Union of Biochemistry, IUB, class 3), chosen from enzymes of the cellulase class (subclass 3.2). These enzymes are also known as glucosidases.

The enzymes are preferably chosen from cellobiohydrolases, endoglucanases, β-glucosidases, hemicellulases, α-amylases, xylanases, β-mannanases, endocellulases, etc., and mixtures of these enzymes, without losing sight of the fact that these enzymes often have secondary activities along with their main activity.

The enzymatic composition used may comprise enzymes of the exocellular or endocellular type.

The enzymes may be of bacterial or fungal origin or of any other possible origin.

The enzymatic composition used may also comprise enzymes of the lipase type (subclass 3.1) and mixtures of these enzymes.

An alternative to this method consists in solubilizing tannins obtained using a conventional extraction method and treating them, in aqueous or aqueous-alcoholic phase, with the enzymatic composition described above. Another subject of the invention is therefore a method for enzymatically transforming tannins obtained conventionally.

A subject of the invention is also an enzymatic composition mainly comprising enzymes of the cellulase class, having at least one activity chosen from endocellulase activities between $10\times10^6$ and $1\times10^9$ ECU (preferably between $30\times10^6$ and $0.3\times10^9$ ECU), xylanase activities between $6\times10^6$ and $0.6\times10^9$ BXU (preferably between $20\times10^6$ and $0.2\times10^9$ BXU), β-mannanase activities between $4\times10^6$ and $0.4\times10^9$ MNU (preferably between $10\times10^6$ and $0.1\times10^9$ MNU) and α-amylase activities between $10\times10^6$ and $1\times10^9$ αTU (preferably between $30\times10^6$ and $0.3\times10^9$ αTU). All these activities are expressed per tonne of wood to be treated. A subject of the invention is also the methods for extracting or transforming tannins using a composition of enzymes as described above.

The methods according to the invention have proved to allow hydrolysis of the soluble ellagitannins naturally present in wood, and also of some of the ellagitannins bound to the parietal polysaccharides, and of various aromatic molecules, such as digallic acid or heteroside coumarins.

The methods according to the invention therefore make it possible to improve the impact on taste of the wood extracts by eliminating a significant portion of the undesirable compounds (such as certain phenol compounds) and hydrolyzing forms judged to be bitter or astringent.

Depending on whether neutral or acid cellulases are used, the pH is adjusted to between 3 and 8, preferably between 4 and 7. The temperature of the bath is maintained constant between 20 and 90° C., preferably between 40 and 60° C. The treatment by immersion may last for 5 minutes to 2 weeks, preferably for between 1 hour and 24 hours, depending on the support chosen, on the volume to be treated, on the volume of the bath, on the temperature and on the pH.

After this treatment by immersion, the bath is filtered and the liquid is evaporated, preferably lyophilized.

DETAILED DESCRIPTION OF THE INVENTION

Materials and Methods

1. Origin of the Wood Samples

The samples are obtained from hard-wood transformed into duramen. The samples to be treated (nutgall, oak, chestnut, etc.) according to the invention are simply dried in a dryer (1 month, 40° C., with ventilation). The various randomly taken samples are planed down and then reduced to sawdust by grinding in liquid nitrogen, before being sieved so as to keep only the particles less than 250 μm in size. The samples are conserved after lyophilization, to be analyzed within a period of 2 months.

2. Preparation of the Extracts and Monitoring of Their Composition 1 g of sawdust (250 μm) is subjected to extraction with 100 ml of solvent (acetone/water 7:3 by volume) for 12 h at ambient temperature on a shaking platform; the extract obtained is then filtered through a membrane, lyophilized and weighed.

100 μg of lyophilized extract are used to identify the major ellagitannins by LSIMS mass spectrometry.

1 mg of the extract is taken up with methanol/water (6:4) in order to be analyzed by HPLC coupled to a UV-detector and to an LSIMS mass spectrometer, according to the device developed by Vivas et al. (1995). The HPLC separation method is described in the following paragraph.

3. Assaying the Phenol Compounds

3.1. Coumarins

The coumarins are quantitatively extracted with diethyl ether from 20 ml of wood extract. The organic phase is evaporated to dryness and the residue is taken up with methanol. The HPLC analysis is carried out using a Varian 5060 coupled to a spectrofluorometric detector (Kontron SFM23/B) and an Ultrasphere ODS column. The pure coumarins were supplied by Extrasynthesis (esculin, esculetin, scopoletin, ombelliferone, methylombelliferone) and Sigma (sporalen). The coumarins are observed by fluorescence (excitation 425 nm and emission 325 nm).

3.2. Ellagitannins

3.2.1. Reference Products

Vescalagin and castalagin are isolated and purified from the duramen of Q. robur, under the conditions described by Vivas et al. (1995). The various roburins (A-E) and grandinin come from Scalbert (INA/INRA Thierval-Grignon).

3.2.2. Separation and Assaying of Ellagitannins by HPLC

The chromatographic technique for separating and assaying the ellagitannins is in accordance with the method developed by Scalbert et al. (1990). The wood extracts are analyzed by HPLC on an Ultrasphere ODS column. Detection is carried out at $\lambda=280$ nm.

3.2.3. Assaying of Total Ellagitannins

Estimation of the Level of Total Phenol Compounds

The richness of the wood extracts in total phenol compounds is estimated either by the method using the Folin-Ciocalteu reagent or by measuring the absorbence at 280 nm of the extracts diluted 100-fold (Vivas et al., 1993). These two methods give results which are comparable but not specific for ellagitannins.

Reaction of Oxidation with Nitrous Acid

In this method proposed by Bate-Smith (1972), esters of hexahydroxyphenic acid and of glucose are oxidized with nitrous acid under nitrogen. The reaction produces a blue coloration which is measured at 600 nm. The results are estimated in mg/g of castalagin equivalent ($\epsilon_{600\ nm}$: 983 g$^{-1}$)

Acid Degradation

The method proposed is adapted from that developed by Peng et al. (1991). It is based on the acid hydrolysis of ellagitannins, followed by assaying the ellagic acid released, by HPLC. The results are expressed in mg/g of castalagin equivalent, taking one mole of castalagin as giving, under these conditions, one mole of ellagic acid (Peng et al., 1991).

4. Extraction and Assaying of Polysaccharides

4.1. Study of the Polysaccharide Fraction of the Control Samples and Treated Samples

4.1.1. Extraction of Polysaccharides 139 g of dry sawdust are left to soak for 72 h in water, on a shaking platform at ambient temperature. The solution is then filtered and then centrifuged. The extract is then concentrated to 500 ml.

4.1.2. Isolation of Polysaccharides

The extracts undergo 3 precipitations (one at 1:9 water/ethanol at 95% vol., two at 1:5 of the same mixture). The precipitation is carried out at 3° C. for 12 h. The fractions are then lyophilized.

4.1.3. Partial Characterization

The precipitate has a fluffy appearance, very pale in color, slightly gray, which is probably a complex with the ellagitannins from which it is difficult to isolate the polysaccharide fraction.

4.1.4. Assaying Using a Chemical Method

Assaying of Neutral Polysaccharides (nP)

The neutral polysaccharides are assayed using the sulfuric phenol method. The optical density is read at 490 nm and the results are expressed in mg/l of glucose equivalent.

Assaying of Acid Polysaccharides (aP)

The acid polysaccharides are assayed using the meta-phenylphenol method. The optical density is measured at 520 nm and the results were expressed in mg/l of galacturonic acid equivalent.

4.2. Extraction and Assaying of Polysaccharides From Wood 1 g of woodchips is left to soak for 24 h in water at 20° C. on a shaking platform. The solution is collected by filtration and centrifuged. The sawdust recovered is then dried and left to soak once again in a 5% sodium hydroxide solution under the same conditions. The alkaline solution is also collected by filtration and centrifuged. 95% ethanol is then added to the two categories of extract (water and sodium hydroxide), in a proportion of 1:5 by volume. The polysaccharides are then collected by centrifugation and taken up with distilled water at 60° C. The nPs are assayed with sulfuric phenol and the aPs are assayed with meta-phenylphenol. The reference solutions are, respectively, an aqueous solution of glucose at 100 mg/l and an aqueous solution of galacturonic acid at 50 mg/l for nP and aP.

EXAMPLES

Example 1

5000 l of water and 5 kg of enzymatic composition having an endocellulase activity of $0.1\times10^9$ ECU, a xylanase activity of $0.18\times10^9$ BXU, a β-mannanase activity of $36\times10^6$ MNU and an α-amylase activity of $0.21\times10^9$ αTU are added to a tank containing 1000 kg of oak sawdust. The pH is adjusted to 5.0 with citric acid and the temperature is raised to 60° C. After treatment for 24 h, the tank is emptied and the liquid is filtered and then lyophilized.

After this treatment, the main groups of compounds were fractionated and the various fractions were compared relative to an untreated control.

To carry out this fractionation, the oak wood extract is evaporated to dryness. The dry extract obtained is taken up with a volume of water, with shaking for 2 hours at 30° C. The insoluble fraction obtained comprises the lignins. The soluble fraction is again evaporated to dryness. The dry extract is then taken up with a volume of an ethanol/water mixture (9:1 by volume) and kept at 4° C. for 12 h. The insoluble fraction obtained comprises the polysaccharides. With regard to the soluble fraction, it comprises the ellagitannins. In the treated sawdust, the dry extract represents 4.2% by weight relative to the wood, against 12.3% by weight for the untreated wood control. The weight percentages of each of the three fractions relative to the dry extract are given in table I.

TABLE I

|  | Ellagitannins | Polysaccharides | Lignins |
|---|---|---|---|
| Control | 60% | 30% | 10% |
| Treated according to the invention | 35% | 50% | 15% |

This experiment made it possible to demonstrate hydrolysis of the ellagitannins, in parallel with a relative increase in the polysaccharide content, in the dry extract.

These various fractions were then subjected to more precise assays, demonstrating a decrease in extractable solids, in ellagitannins, in proanthocyanidins and in glycosylated coumarins (see table II).

TABLE II

| Results in mg/g of sawdust | Control | Treated according to the invention |
|---|---|---|
| Dry extract | 123 | 42 |
| Ellagitannins | 54 | 21 |
| Proanthocyanidins | 0.62 | 0.12 |
| Coumarins: | | |
| glycosylated coumarins (esculin + scopolin) | 5.7 | 1.4 |
| aglycone coumarins (esculetin + scopoletin) | 1.3 | 6.8 |

A substantial increase in the polysaccharides was also noted in another experiment in which the assay made it possible to distinguish between the nP and aP polysaccharides (see table III).

TABLE III

| | Soluble polysaccharides (mg/g of sawdust) | |
|---|---|---|
| | Neutral (nP) | Acid (aP) |
| Control | 370 | 25 |
| Treated according to the invention | 625 | 48 |

The treatment therefore makes it possible to eliminate certain substances judged to be undesirable due to their astringent characteristic (such as castalagin) or bitter characteristic (such as esculin), and to transform them into neutrally tasting molecules (such as gallic acid, ellagic acid and, to a lesser extent, esculetin), and also to increase the polysaccharide content (which will tend to make wine matured in the presence of this wood extract fuller and fatter).

A series of taste tests was also carried out (see table IV). They confirm the above experiments in the sense that the amount of wood extract required to detect the bitter or astringent characteristics is much higher in the case of sawdust treated enzymatically according to the invention, compared to untreated sawdust.

TABLE IV

Comparison of the taste detection thresholds as a function of the treatment method, indicating the taste detection threshold $(T_{50\%})$* in mg/l of model wine solution

| | Astringency | Bitterness |
|---|---|---|
| Untreated sawdust | 130 | 110 |
| Sawdust treated according to the invention | 420 | 350 |

*$T_{50\%}$: concentration starting from which a substance is detected by 50% of tasters.

Example 2

1000 kg of oak sawdust are replaced with 1000 kg of chestnut sawdust in 5000 l of water, and the procedure is carried out with 5 kg of the enzymatic composition described in example 1.

Extracts of chestnut (rich in digallic acid derived from hydrolysis of the gallotannins) from diverse origins were subjected (see table V) to enzymatic hydrolysis with the enzymatic preparation according to the invention.

Virtually total hydrolysis of the digallic acid to gallic acid emerges from this, as does a large decrease in the glycosylated coumarins (the aglucone coumarins being insipid).

These results are of great importance since they show the possibility of enhancing the value of a species which has been used very little to date. Chestnut in fact has all the qualities required in oenology, but is used very little because of the considerable bitterness which it produces.

The enzymatic treatment decreases this bitterness a great deal and makes it possible to envision chestnut being used more, for specific uses in which oak is not suitable. Thus, for maturing colorless spirits, chestnut is entirely indicated because, since it has no ellagitannins, it will barely modify the fruit taste of the alcohol and, since it has no pigments, neither will it color the alcohol to be treated.

TABLE V

Enhancement of the value of chestnut through the use of the enzymatic preparation according to the invention

| Results in mg/g of sawdust | Digallic acid | Glycosylated coumarins |
|---|---|---|
| | Control | |
| Dordogne chestnut | 10.2 | 8.3 |
| Dauphiné chestnut | 9.3 | 5.7 |
| Gironde chestnut | 4.6 | 10.2 |
| | Treated according to the invention | |
| Dordogne chestnut | <0.1 | 2.3 |
| Dauphiné chestnut | 0.4 | 1.7 |
| Gironde chestnut | 0.8 | 3.5 |

The invention claimed is:

1. A method for producing oenological tannins from lumps of wood, which comprises the steps of bringing the wood into contact with an aqueous enzymatic composition containing one or more cellulase class enzymes; filtering the composition to obtain a liquid extract therefrom; and lyophylizing the liquid extract to afford a solid composition comprising oenological tannins; wherein the enzymatic composition comprises one or more enzymes selected from the group consisting of cellobiohydrolases, endoglucanases, β-glucosidases, hemicellulases, α-amylases, xylanases, β-mannanases, endocellulases, and mixtures of these enzymes; wherein the enzymatic composition comprises an endocellulase activity, a xylanase activity, a β-mannanase activity, and an α-amylase activity, and includes one or more enzyme activities selected from the group consisting of: an endocellulase activity between $10 \times 10^6$ and $1 \times 10^9$ ECU per tonne of wood to be treated, a xylanase activity between $6 \times 10^6$ and $0.6 \times 10^9$ BXU per tonne of wood to be treated, a β-mannanase activity between $4 \times 10^6$ and $0.4 \times 10^9$ MNU per tonne of wood to be treated and an α-amylase activity between $10 \times 10^6$ and $1 \times 10^9$ αTU per tonne of wood to be treated.

2. The method of claim 1, wherein the wood is brought into contact with the enzymatic composition by immersion in the composition for a period of time ranging from 5 minutes to 2 weeks.

3. The method of claim 1, wherein the pH of the composition is between 3 and 8.

4. The method of claim 1, wherein the temperature of the composition is between 20 and 90° C.

5. The method of claim 1, wherein the lumps of wood are in the form of sawdust.

6. The method of claim 1, wherein the lumps of wood are in the form of woodchips.

7. A method for transforming tannins obtained by extraction of wood with solvent to oenological tannins, the method comprising contacting the tannins with an aqueous enzymatic composition containing one or more cellulase class enzymes to form an oenological tannin extract; filtering the tannin extract to obtain a filtrate; and lyophylizing the filtrate to form a solid composition comprising oenological tannins; wherein the enzymatic composition comprises one or more enzymes selected from the group consisting of cellobiohydrolases, endoglucanases, β-glucosidases, hemicellulases, α-amylases, xylanases, β-mannanases, endocellulases, and mixtures of these enzymes; wherein the enzymatic composition comprises an endocellulase activity, a xylanase activity, a β-mannanase activity, and an α-amylase activity, and includes one or more enzyme activities selected from the group consisting of: an endocellulase activity between $10 \times 10^6$ and $1 \times 10^9$ ECU per tonne of wood to be treated, a xylanase activity between $6 \times 10^6$ and $0.6 \times 10^9$ BXU per tonne of wood to be treated, a β-mannanase activity between $4 \times 10^6$ and $0.4 \times 10^9$ MNU per tonne of wood to be treated and an α-amylase activity between $10 \times 10^6$ and $1 \times 10^9$ αTU per tonne of wood to be treated.

8. An enzymatic composition for producing oenological tannins, comprising enzymes of the cellulase class, and which comprises an endocellulase activity, a xylanase activity, a β-mannanase activity, and an α-amylase activity, and includes one or more enzyme activities selected from the group consisting of: an endocellulase activity between $10 \times 10^6$ and $1 \times 10^9$ ECU per tonne of wood to be treated, a xylanase activity between $6 \times 10^6$ and $0.6 \times 10^9$ BXU per tonne of wood to be treated, a β-mannanase activity between $4 \times 10^6$ and $0.4 \times 10^9$ MNU per tonne of wood to be treated and an α-amylase activity between $10 \times 10^6$ and $1 \times 10^9$ αTU per tonne of wood to be treated.

9. The method of claim 1, wherein the wood is chestnut wood.

10. The method of claim 7, wherein the tannins obtained by extraction of wood with a solvent are chestnut wood tannins.

11. The method of claim 1 wherein the wood is oak.

12. The method of claim 1 wherein the wood is chestnut.

* * * * *